US00RE37336B1

(19) United States
(12) Reissued Patent
Weigel et al.

(10) Patent Number: US RE37,336 E
(45) Date of Reissued Patent: Aug. 21, 2001

(54) METHOD FOR PROVIDING HYALURONIC ACID

(75) Inventors: Paul H. Weigel, Edmond, OK (US); John Papaconstantinou, Galveston, TX (US)

(73) Assignee: The Board of Regents of the University of Oklahoma, Norman, OK (US)

(21) Appl. No.: 09/281,107

(22) Filed: Mar. 29, 1999

Related U.S. Patent Documents

Reissue of:
(64) Patent No.: 5,015,577
Issued: May 14, 1991
Appl. No.: 07/401,316
Filed: Aug. 29, 1989

(51) Int. Cl.[7] ..... C12P 19/04; C12N 1/21; C12N 9/10; C07H 15/12

(52) U.S. Cl. ..... 435/101; 435/252.3; 435/252.33; 435/253.4; 435/320.1; 435/849; 435/885; 435/193; 536/23.7

(58) Field of Search ..... 536/23.2, 23.7; 435/101, 193, 252.3, 252.33, 253.4, 320.1, 849, 885

(56) References Cited

U.S. PATENT DOCUMENTS

| | | | | |
|---|---|---|---|---|
| 4,517,295 | * | 5/1985 | Bracke et al. | 435/885 |
| 4,529,797 | * | 7/1985 | Peik et al. | 435/104 |
| 4,535,153 | * | 8/1985 | Kang et al. | 435/104 |
| 4,647,657 | * | 3/1987 | Wan | 536/123 |
| 4,713,449 | * | 12/1987 | Vanderslice et al. | 536/123 |
| 4,782,046 | | 11/1988 | Brown et al. | 514/54 |
| 4,784,990 | | 11/1988 | Nimrod et al. | 514/54 |
| 4,801,539 | * | 1/1989 | Akasaka et al. | 435/885 |

FOREIGN PATENT DOCUMENTS

| | | | | |
|---|---|---|---|---|
| 8800948 | * | 7/1987 | (WO) | 435/101 |

OTHER PUBLICATIONS

Eisenbeis et al., Strains of *E. coli* carrying the structural gene for histidyl tRNA synthetase on a high copy number plasmid. Mol. Gen. Genet. 183–115–122, 1981.*

Tsui et al., Isolation, structure and expression of mammalian genes for histodyl–tRNA synthetase. Nuc. Acids Res. 15(8):3349–3367, 1987.*

Okita et al. J. Biol. Chem. 256(13):6944–6952 (1981).*

MacLennan, A.P., J. Gen. Microbiol., 14:134–142 (1956).

MacLennan, A.P., J. Gen. Microbiol., 14:143–152 (1956).

Markovitz, A., et al, J. of Biol. Chem., 234(9):2343–2350 (1959).

Markovitz, A., et al, J. Biol. Chem., 237(2):273–279 (1962).

Stoolmiller, A. et al., J. of Biol. Chem., 244(2):236–246 (1969).

Sugahara, K. et al., J. of Biol. Chem., 254(14):6252–6261 (1979).

Van De Rijn, I., J. of Bacteriology, 156(3):1059–1065 (1983).

Prehm, P., Atricular Cartlidge Biochemistry, edited by K. Kuettner, et al., Raven Press, N.Y. 81–91 (1986).

Prehm, P., et al., Biochem. J. 235:887–889 (1986).

Triscott, M., et al., J. of Biol. Chem., 261(13):6004–6009 (1986).

Dialog Search Report.

Computer Search Report.

* cited by examiner

*Primary Examiner*—Stephanie W. Zitomer
(74) *Attorney, Agent, or Firm*—Dunlap, Codding & Rogers, P.C.

(57) ABSTRACT

Disclosed are DNA segments encoding [hyaluronic acid synthase which are employed to construct recombinant cells useful in the production of hyaluronate synthase or hyaluronic acid (HA)] *the recombinant DNA segment identified in FIG. 5.* In preferred aspects, chromosomal DNA from Streptococcus equisimilis is partially digested with EcoRI and the resultant fragments are ligated to form recombinant vectors. These vectors are useful in the transformation of host cells such as *E. coli* and or Streptococcal hosts. [Resultant transformants are screened by the novel screening assays to identify colonies which have incorporated HA synthase DNA in a form that is being actively transcribed into the corresponding HA synthase enzyme. These colonies may be selected and employed in the production of the enzyme itself or its product, HA.] *The recombinant DNA segment identified in FIG. 5 is then inserted into a recombinant Streptococcal host for the production of hyaluronic acid (HA).*

1 Claim, 5 Drawing Sheets

FIG.4A
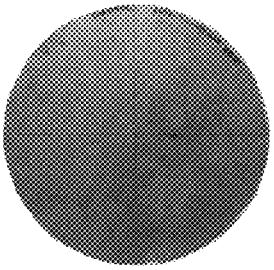
FIG.4B
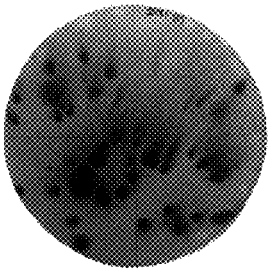
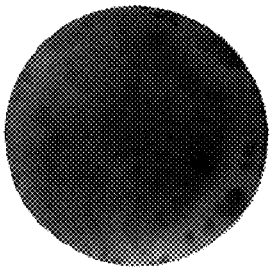
FIG.4C
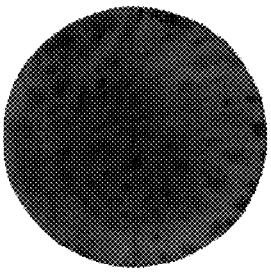
FIG.4D
FIG.5
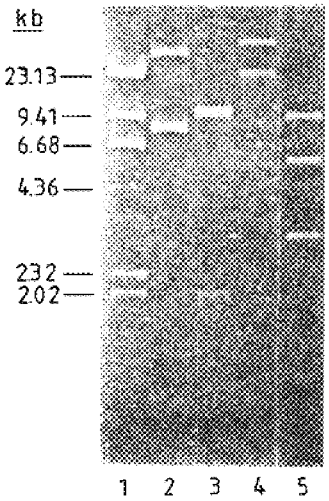

METHOD FOR PROVIDING HYALURONIC ACID

Matter enclosed in heavy brackets [ ] appears in the original patent but forms no part of this reissue specification; matter printed in italics indicates the additions made by reissue.

The government may own rights in the present invention pursuant to NIH Grant GM 35978.

BACKGROUND OF THE INVENTION

1. Field of the Invention

The present invention relates to [DNA encoding the enzyme hyaluronate synthase, and to the use of this DNA in the preparation of recombinant cells for the production of the hyaluronate synthase enzyme and/or hyaluronic acid] *a method for providing hyaluronic acid.*

2. Description of the Related Art

The incidence of Streptococcal infections is a major health and economic problem worldwide, particularly in the developing countries (21). One reason for this is due to the ability of Streptococcal bacteria to often grow undetected by the body's phagocytic cells (i.e., macrophages and polymorphonuclear cells (PMNs). These cells are responsible for recognizing and engulfing foreign microorganisms. One effective way by which the bacteria evade surveillance is by coating themselves with polysaccharide capsules, such as hyaluronic acid (HA) capsules. Since polysaccharides are generally nonimmunogenic, the encapsulated bacteria do not elicit an immune response and are, therefore, not targeted for destruction. Moreover, the capsule exerts an antiphagocytic effect on PMNs in vitro (7) and prevents attachment of Streptococcus to macrophages (32). Precisely because of this, in group A and group C Streptococci, the HA capsules are major virulence factors in natural and experimental infections (9,10). The group C Streptococcus equisimilis is responsible for osteomyelitis (1), pharyngitis (2), brain abscesses (5), and pneumonia (20,25).

Structurally, HA is a high molecular weight linear polysaccharide of repeating disaccharide units consisting of N-acetylglucosamine (GlcNAc) and glucuronic acid (GlcUA). HA is the only glycosaminoglycan synthesized by both mammalian and bacterial cells particularly groups A and C Streptococci. Some Streptococcus strains make HA which is secreted into the medium as well as HA capsules. The mechanism by which these bacteria synthesize HA is of interest since the production of the HA capsule is a very efficient and clever way by which Streptococci evade surveillance by the immune system.

HA is synthesized by both mammalian and Streptococcus cells by the enzyme hyaluronate synthase, which has been localized to the cytoplasmic membrane of Streptococcus (14). The synthesis of HA in these organisms is a multi-step process. Initiation involves binding of the first precursor, UDP-GlcNAc or UDP-GlcUA. This is followed by elongation which involves alternate addition of the two sugars to the growing oligosaccharide chain. The growing polymer is extruded across the bacterial plasma membrane and region of the cell wall and into the extracellular space. Although the HA biosynthetic system was one of the first membrane heteropolysaccharide synthetic pathways studied, the mechanism of HA synthesis is still not understood (29). This may be because in vitro systems developed to date are inadequate in that de novo biosynthesis of HA has not been accomplished. Chain elongation but not initiation occurs.

The direction of HA polymer growth is a matter of disagreement. Addition of the monosaccharides could be to the reducing (17) or nonreducing (26) end of the growing HA chain. In addition, other questions that need to be addressed are (i) whether nascent chains are linked covalently to a protein, to UDP or to a lipid intermediate, (ii) whether chains are initiated using a primer, and (iii) the mechanism by which the mature polymer is extruded through the plasma membrane of the Streptococcus. Understanding the mechanism of HA biosynthesis may allow development of alternative strategies to control Streptococcal infections by interfering in the process.

S. equisimilis strain D181 synthesizes and secretes HA. Investigators have used this strain and a group A strain A111 to study the biosynthesis of HA and to characterize the HA-synthesizing activity in terms of its divalent cation requirement (26), precursor (UDP-GlcNAc and UDP-GlcUA) utilization (8,13), optimum pH (26), and molecular weight (18). Although a 52-kD protein has been identified as the HA synthase (18), no one has successfully purified to homogeneity an active enzyme. Moreover, it's not clear whether this molecule is all that is needed for the generation of hyaluronic acid, or whether it might act in concert with other cellular components or subunits. Thus, totally ex vivo methods of producing HA have not been forthcoming.

Typically, HA has been prepared commercially by isolation from either rooster combs or extracellular media from Streptococcal cultures. One method which has been developed for preparing HA is through the use of cultures of HA-producing streptococcal bacteria U.S. Pat. No. 4,517,295, describes such a procedure, wherein HA-producing Streptococci are fermented under anaerobic conditions in a $CO_2$-enriched growth medium. Under these conditions, HA is produced and can be extracted from the broth. It is generally felt that isolation of HA from rooster comb is laborious and difficult, since one starts with HA in a less pure state. The advantage of isolation from rooster comb is that the HA produced is of higher molecular weight. However, preparation of HA by bacterial fermentation is easier, since the HA is of higher purity to start with. Usually, however, the molecular weight of HA produced in this way is smaller than that from rooster combs. Therefore, a technique that would allow the production of high molecular weight HA by bacterial fermentation Would be an improvement over existing procedures.

High molecular weight HA has a wide variety of useful applications—ranging from cosmetics to eye surgery. Due to its potential for high viscosity and its high biocompatability, HA finds particular application in eye surgery as a replacement for vitreous fluid. HA has also been used to treat racehorses for traumatic arthritis by intra-articular injections of HA, in shaving cream as a lubricant, and in a variety of cosmetic products due to its physiochemical properties of high visocity and its ability to retain moisture for long periods of time. In general, the higher molecular weight the HA that is employed the better. This is because HA solution viscosity increases with the average molecular weight of the individual HA polymer molecules in the solution. Unfortunately, very high molecular weight HA, such as that ranging up to $10^7$, has been difficult to obtain by currently available isolation procedures.

To address these or other difficulties, there is a need for new methods and constructs which can be used to produce HA having one or more improved properties such as greater purity or ease of preparation. In particular, there is a need to develop methodology for the production of larger amounts of relatively higher molecular weight and purity HA than is available from current technology. The present invention addresses one or more shortcomings in the art through the application of recombinant DNA technology.

SUMMARY OF THE INVENTION

The present invention involves the application of recombinant DNA technology to solving one or more problems in the art of hyaluronic acid preparation. These problems are addressed through the isolation and use of a *recombinant* DNA segment [encoding all or a portion of the hyaluronate synthase gene, the gene responsible for HA chain biosynthesis] *identified in FIG. 5*. The [gene] *recombinant segment* is cloned from DNA of an appropriate tissue or cellular source and engineered into useful recombinant constructs [for the preparation of HA and for the preparation of large quantities of the HA synthase enzyme itself].

Through the application of techniques set forth herein, those of skill in the art will be enabled to obtain *a recombinant* DNA [segments encoding all or a portion of the HA synthase gene] *segment identified in FIG. 5*. Through isolation of [the HA gene] *this DNA,* from whatever source is chosen, one will have the ability to realize significant advantages such as an ability to manipulate the host that is chosen to express the [HA synthase gene] *recombinant DNA segment identified in FIG. 5,* the fermentation environment chosen for HA production, as well as genetic manipulation of the underlying gene. As those of skill in the art will recognize in light of the present disclosure, this will provide additional significant advantages both in the ability to control the expression of the gene and in the nature of the gene product that is realized.

Accordingly, in a general and overall sense, the invention is directed to the isolation of DNA that comprises the [HA synthase gene] *recombinant DNA segment identified in FIG. 5*, whether it be from prokaryotic or eukaryotic sources. This is possible because the [enzyme, and indeed the gene,] *recombinant segment* is one found in both eukaryotes and some prokaryotes. Typical prokaryotic sources will include Group A or Group C Streptococcal sources such as S. equisimilis, S. zooepidemicus, or S. pyogenes. Eukaryotes are also known to produce HA and thus have HA synthase genes that may be employed in connection with the invention. For example, it is known that HA is produced in rooster combs by mesodermal cells of the rooster. These cells can be employed to isolate starting mRNA for the production of cDNA clone banks by well known techniques, which can subsequently be screened by novel screening techniques set forth herein. Other eukaryotic sources which can be employed include synovial fibroblasts, dermal fibroblasts, and even trabecular-meshwork cells of the eye.

[HA synthase-encoding] *The recombinant* DNA [segments] *segment identified in FIG. 5* of the present invention [are] *is* defined operationally as [segments] *a recombinant segment* of DNA, isolated free of total chromosomal or genomic DNA such that [they may] *it may* be readily manipulated by recombinant DNA techniques. Accordingly, as used herein, the phrase "substantially purified DNA segment" refers to a *recombinant* DNA segment isolated free of total chromosomal or genomic DNA and retained in a state rendering it useful for the practice of recombinant techniques, such as DNA in the form of a discrete isolated DNA fragment, or a vector (e.g., plasmid, phage or virus) incorporating such a fragment.

Due to certain advantages associated with the use of prokaryotic sources, one will likely realize the most advantages upon isolation of the [HA synthase gene] *recombinant DNA segment identified in FIG. 5* from prokaryotes such as S. equisimilis. One such advantage is that, typically, eukaryotic enzymes may require significant post-translational modifications that can only be achieved in a eukaryotic host. This will tend to limit the applicability of any eukaryotic [HA synthase gene] *recombinant DNA segment identified in FIG. 5* that is obtained. Moreover, those of skill will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library and (b) the ease of manipulation because the overall size of the coding region of a prokaryotic gene is significantly smaller due to the absence of introns. Furthermore, if the product of the [HA synthase gene] *recombinant DNA segment identified in FIG. 5* (i.e., the enzyme) requires post-translational modifications, these would best be achieved in a similar prokaryotic cellular environment (host) from which the [gene] *DNA* was derived.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned. For example, in the preferred recombinant host, Streptococcal hosts, the preferred control region is the homologous control region associated with the structural gene in its natural state. The homologous control region, in fact, may be coisolated directly with the isolation of the [HA synthase structural gene] *recombinant DNA segment identified in FIG. 1* itself through the practice of certain preferred techniques disclosed herein.

Where one desires to use a host other than Streptococcus, it may be advantageous to employ a prokaryotic system such as E. coli, or even eukaryotic systems such as yeast or CHO, African green monkey, VERO cells, or the like. Of course, where this is undertaken, it will generally be desirable to bring the [HA synthase gene] *recombinant DNA segment identified in FIG. 5* under the control of sequences which are functional in the selected alternative host. The appropriate DNA control sequences, as well as their construction and use, are generally well known in the art as discussed in more detail herein below.

In preferred embodiments, the [HA synthase-encoding DNA segments] *recombinant DNA segment identified in FIG. 5* further [include] *includes* DNA sequences, known in the art functionally as origins of replication or "replicons", which allow replication of contiguous sequences by the particular host. Such origins allow the preparation of extrachromosomally localized and replicating chimeric segments or plasmids, to which [HA synthase DNA sequences are] *the recombinant DNA segment identified in FIG. 5 is* ligated. In more preferred instances, the employed origin is one capable of replication in Streptococcal hosts. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning in a number of higher organisms, are well known. In certain embodiments, the invention may thus be defined in terms of a recombinant transformation vector which includes the [HA synthase gene sequence] *recombinant DNA segment identified in FIG. 5* together with an appropriate replication origin and under the control of selected control regions.

In accordance with the present invention, [the HA synthase gene] *recombinant DNA segment identified in FIG. 5,* when from a prokaryotic source such as a Streptococcal source, is obtained by the following general steps. First, genomic DNA is obtained from Streptococcal cells which are capable of producing the enzyme, such as S. equisimilis strain D181. This DNA is then partially digested with a selected restriction enzyme, such as EcoRI, to provide fragments having an average length that is compatible with the insert length allowed by the cloning vector that is subsequently employed. Due to the size of the [HA synthase enzyme] *recombinant DNA segment identified in FIG. 5,* one will desire to obtain DNA that has an average length of up to 15 kb, and preferably about 5–10 kb. The use of the partial digestion technique is a significant factor in the practice of the invention in that it avoids the potential problem of an incomplete gene that will be realized if the selected enzyme gene has a restriction enzyme [site within the HA synthase coding region].

Thus, although the present invention is exemplified in terms of EcoRI digestion, it will be appreciated by those of skill in the art that the invention is in no way limited to EcoRI digestion fragments. For example, in that digestions are partial, DNA fragments may be obtained which contain full complements of genes. DNA fragments so-produced are random in that under partial restriction digestion conditions, not every enzyme recognition site is recognized and cleaved. The fact that a selected restriction enzyme recognition site may be present within, for example, a particular desired coding sequence does not limit the usefulness of partial enzyme digestion as a method for fragmenting the DNA because at least a proportion of the population of the DNA fragments will provide a full, uncleaved sequence of the particular gene. Virtually any restriction enzyme may be employed for the generation of DNA fragments in accordance with the present invention. Thus, the only limitation generally on the particular restriction enzyme employed for DNA fragmentation is that such enzyme should preferably be compatible with cloning sites present in the particular cloning vehicle employed.

Once the DNA has been partially digested, it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pSA3, lambda, SV40, polyoma, adenovirus, bovine papilloma virus and retroviruses. However, it is believed that particular advantages will ultimately be realized where vectors capable of replication in both Streptococcal strains and E. coli are employed.

Vectors such as these, exemplified by the pSA3 vector of Dao and Ferretti (4), allow one to perform clonal colony selection in an easily manipulated host such as E. coli, followed by subsequent transfer back into a Streptococcal strain for production of HA. This is advantageous in that one can augment the Streptococcal strain's inherent ability to synthesize HA through gene dosaging (i.e., providing extra copies of the [HA synthase gene] *recombinant DNA segment identified in FIG. 5* by amplification). The inherent ability of the streptococci to synthesize HA can also be augmented through the formation of extra copies, or amplification, of the plasmid that carries the [HA synthase gene] *recombinant DNA segment identified in FIG. 5.* This amplification can account for up to a 10-fold increase in plasmid copy number and, therefore, the [HA synthase gene] *recombinant DNA segment identified in FIG. 5* copy number.

Another procedure that would further augment [HA synthase gene] *the recombinant DNA segment identified in FIG. 5* copy number is the insertion of multiple copies [of the gene] into the plasmid. This extra amplification would be especially feasible if the [bacterial HA synthase gene] size *of the recombinant DNA segment identified in FIG. 5* is small. In any event, the chromosomal DNA-ligated vector is employed to transfect the host that is selected for clonal screening purposes such as *E. coli,* through the use of a vector that is capable of expressing the inserted DNA in the chosen host.

Where a eukaryotic source such as dermal or synovial fibroblasts or rooster comb cells is employed, one will desire to proceed initially by preparing a cDNA library. This is carried out first by isolation of mRNA from the above cells, followed by preparation of double stranded cDNA using reverse transcriptase and ligation with the selected vector. Numerous possibilities are available and known in the art for the preparation of the ds cDNA, and all such techniques are believed to be applicable. A preferred technique involves reverse transcription. Once a population of ds cDNAs is obtained, a cDNA library is prepared in the selected host by accepted techniques, such as by ligation into the appropriate vector and amplification in the appropriate host. Due to the high number of clones that are obtained, and the relative ease of screening large numbers of clones by the techniques set forth herein, one may desire to employ phage expression vectors, such as lambda gt11 or gt12, for the cloning and expression screening of cDNA clones.

Due to the general absence of information regarding the [HA synthase gene] *recombinant DNA segment identified in FIG. 5,* traditional approaches to clonal screening, such as oligonucleotide hybridization or immunological screening, is not available. Accordingly, it was necessary for the inventors to develop novel approaches to colony screening which rely on the expression of the inserted [HA synthase] *recombinant* DNA *segment identified in FIG. 5.* The methods which were developed can be applied to screen the selected host, regardless of whether a eukaryotic or prokaryotic gene is sought. One method involves the application of a dye staining technique to identify clones which contain HA. The typical dye employed, alcian blue, binds to and stains polyanionic molecules such as HA. However, in that alcian blue is not entirely specific for HA, one will desire to employ additional screening methods.

An additional method which has been developed employs the binding of a labeled proteoglycan monomer to bacterial cell surfaces. This proteoglycan monomer binds specifically to HA[,] . [the product of the HA synthase enzyme. Some HA synthase molecules on the cell surface may be bound to] HA molecules [they are synthesizing and these complexes] may be present in the membrane or cell walls of host cells[, which have been transformed to express the HA synthase]. Labeled proteoglycan will then bind to the HA, [which is in turn bound to the HA synthase,] *which is bound to the product of the recombinant DNA segment identified in FIG. 5* and thus identify cells or clones expressing the [desired HA synthase enzyme] *recombinant DNA segment identified in FIG. 5.* A variety of additional screening procedures are also set forth herein which can variously be employed to identify the presence [of either the HA enzyme or its HA product] *of the recombinant DNA segment of FIG. 5 or its HA product* as a means for identifying positive clones.

Once a positive clone is identified, and the presence of [putative HA synthase] *the recombinant DNA segment identified in FIG. 5* is confirmed, it will be desirable to subject the cloned insert to restriction enzyme mapping and DNA sequence analysis. This will both identify the amino acid sequence of the underlying [enzyme] *DNA product*, and provide the ability to further engineer the [HA synthase DNA] *recombinant DNA segment identified in FIG. 5*. It is recognized that [HA synthase DNA] *the recombinant DNA segment identified in FIG. 5* may be engineered in a variety of manners and for many purposes. For example, it is possible to tailor the sequence by deletion of a transmembrane spanning domain that would normally insert the [enzyme] *segment product* into the bacterial membrane. Removal of this region or regions from, and possibly addition of a leader signal sequence to [the HA synthase DNA] *recombinant DNA segment identified in FIG. 5* would then direct the completed enzyme to be secreted from the cell into the medium. Furthermore, manipulation and/or alteration of the underlying nucleotide sequences can be achieved to provide for a recombinant enzyme having improved kinetic attributes. Thus, in light of the present disclosure, once the mapping and sequence analysis is complete, those of skill in the art will have the ability to reengineer the gene into desired expression constructs, including positioning the gene to bring it under the control of whatever promoter system that is desired.

For the purposes of the present invention the preferred promoter/vector/host system for subsequent production of HA will be (a) the [normal HA synthase] *recombinant DNA segment identified in FIG. 5* promoter of the constitutive gene; (b) the pSA3 shuttle vector and (c) both S. equisimilis or E. coli hosts. Moreover, other preferred systems include the use of a lac Z promoter in an E. coli host. A hyaluronidase negative (HAase$^-$) Streptococcus could also serve as a host cell and should improve the production of undegraded HA. However, other vector/promoter/host systems known in the art can be employed where desired and still realize advantages in accordance with the invention.

Once the [HA synthase DNA] *recombinant DNA segment identified in FIG. 5* is obtained and engineered into a desired promoter/vector system, one will desire to employ the construct for the preparation of [either the HA synthase enzyme or] HA. This will generally include the steps of (1) providing a recombinant host bearing the recombinant DNA segment [encoding the HA synthase enzyme and capable of expressing the enzyme] *identified in FIG. 5;* (2) culturing the recombinant host in media under conditions that will allow for [transcription of the cloned HA gene and appropriate for] the production of the hyaluronic acid; and (3) separating and purifying the [HA synthase enzyme or the] secreted hyaluronic acid from the recombinant host.

Generally, the conditions appropriate for expression of the [cloned HA synthase gene will] *HA* depend upon the promoter/vector/host system that is employed. For example, where one employs the lac promoter, one will desire to induce transcription through the inclusion of a material that will stimulate lac transcription, such as IPTG. Where other promoters are employed, different materials may need to be included to induce or otherwise up-regulate transcription. In addition to obtaining expression of [the enzyme] *HA*, one will preferably desire to provide an environment that is conducive to HA synthesis by including appropriate substrates [for the enzyme], such N-acetylglucosamine (GlcNAc) and glucuronic acid (GlcUA).

One may further desire to incorporate the [gene] *recombinant DNA segment identified in FIG. 5* in a host which is defective in the enzyme hyaluronidase, so that the *HA* product [synthesized by the enzyme will not be] *is not* degraded in the medium. Furthermore, a host would be chosen to optimize production of HA. For example, a suitable host would be one that produced large quantities of the sugar nucleotide precursors to [support the HA synthase enzyme and allow it to] produce large quantities of HA. Such a host may be found naturally or may be made by a variety of techniques including mutagenesis or recombinant DNA technology. The genes for the sugar nucleotide synthesizing enzymes could also be isolated and incorporated in a vector along with the [HA synthase gene] *recombinant DNA segment identified in FIG. 5*. The host containing these new recombinant genes and synthesizing amplified gene products would then produce large amounts of HA.

In the case where production of [HA synthase] *the recombinant DNA segment identified in FIG. 5* is desired, the enzyme is preferably synthesized in bacteria using the T7 expression system (10). pT5 plasmids containing the [HA synthase gene] *recombinant DNA segment identified in FIG. 5* inserted adjacent to the phi10 promoter are transformed into E. coli stain BL21(DE3)pLysS. In this strain the T7 gene encoding the bacteriophage RNA polymerase is under control of the E. coli lac Z promoter. Therefore, the polymerase can be induced by IPTG and transcription of the [HA synthase gene] *recombinant DNA segment identified in FIG. 5* is, in turn, induced from the phi10 promoter of the pT5 vector.

The means employed for culturing of the host cell is not believed to be particularly crucial. For useful details, one may wish to refer to the disclosure of U.S. Pat. Nos. 4,517,295; 4,801,539; 4,784,990; or 4,780,414; all incorporated herein by reference. Where a prokaryotic host is employed, such as S. equisimilis, one may desire to employ a fermentation of the bacteria under anaerobic conditions in $CO_2$-enriched broth growth media. This allows for a greater production of HA than under aerobic conditions. Another consideration is that Streptococcal cells grown anaerobically do not produce pyrogenic exotoxins.

Once the appropriate host has been constructed, and cultured under conditions appropriate for the production of HA, one will desire to separate the HA so produced. Typically, the HA will be secreted or otherwise shed by the recombinant organism into the surrounding media, allowing the ready isolation of HA from the media by known techniques. For example, HA can be separated from the media by filtering and/or in combination with precipitation by alcohols such as ethanol. Other precipitation agents include organic solvents such as acetone or quaternary organic ammonium salts such as cetyl pyridinium chloride (CPC).

A preferred technique for isolation of HA is described in U.S. Pat. No. 4,517,295 in which the organic carboxylic acid, trichloroacetic acid, is added to the bacterial suspension at the end of the fermentation. The trichloroacetic acid causes the bacterial cell to clump and die and facilitates the ease of separating these cells and associated debris from HA, the desired product. The clarified supernatant is concentrated and dialyzed to remove low molecular weight contaminants including the organic acid. The aforementioned procedure utilizes Millipore TM filtration through filter cassettes containing 0.22 mm pore size filters. Diafiltration is continued until the conductivity of the solution decreases to approximately 0.5 mega-ohms.

The concentrated HA is precipitated by adding an excess of reagent grade ethanol or other organic solvent and the precipitated HA is then dried by washing with ethanol and vacuum dried, lypholized or spray dried to remove alcohol. The HA can then be redissolved in a borate buffer, pH 8, and precipitated with CPC or certain other organic ammonium salts such as CETAB, a mixed trimethyl ammonium bromide solution at 4° C. The precipitated HA is recovered by course filtration, resuspended in 1 M NaCl, diafiltered and concentrated as further described in the above referenced patent. The resultant HA is filter sterilized and ready to be converted to an appropriate salt, dry powder or sterile solution, depending on the desired end use.

BRIEF DESCRIPTION OF THE DRAWINGS

FIG. 4. Alcian blue dye staining of bacterial colonies on filters. A: E. coli HB101 transformed with pSA3; B: Streptococcus D181; C: Clone 1; D: Clone 2.

FIG. 5. Determination of DNA insert size in clone 1 and clone 2. Plasmids were isolated from clone 1 and clone 2 by the boiling lysate method and digested with EcoRI. Lanes are indicted in parentheses. HindIII-digested bacteriophage lambda (1); untreated (2) and EcoRI-digested (3) plasmid from clone 1; untreated (4) and EcoRI-digested (5) plasmid from clone 2.

DETAILED DESCRIPTION OF THE PREFERRED EMBODIMENTS

Figure 1:
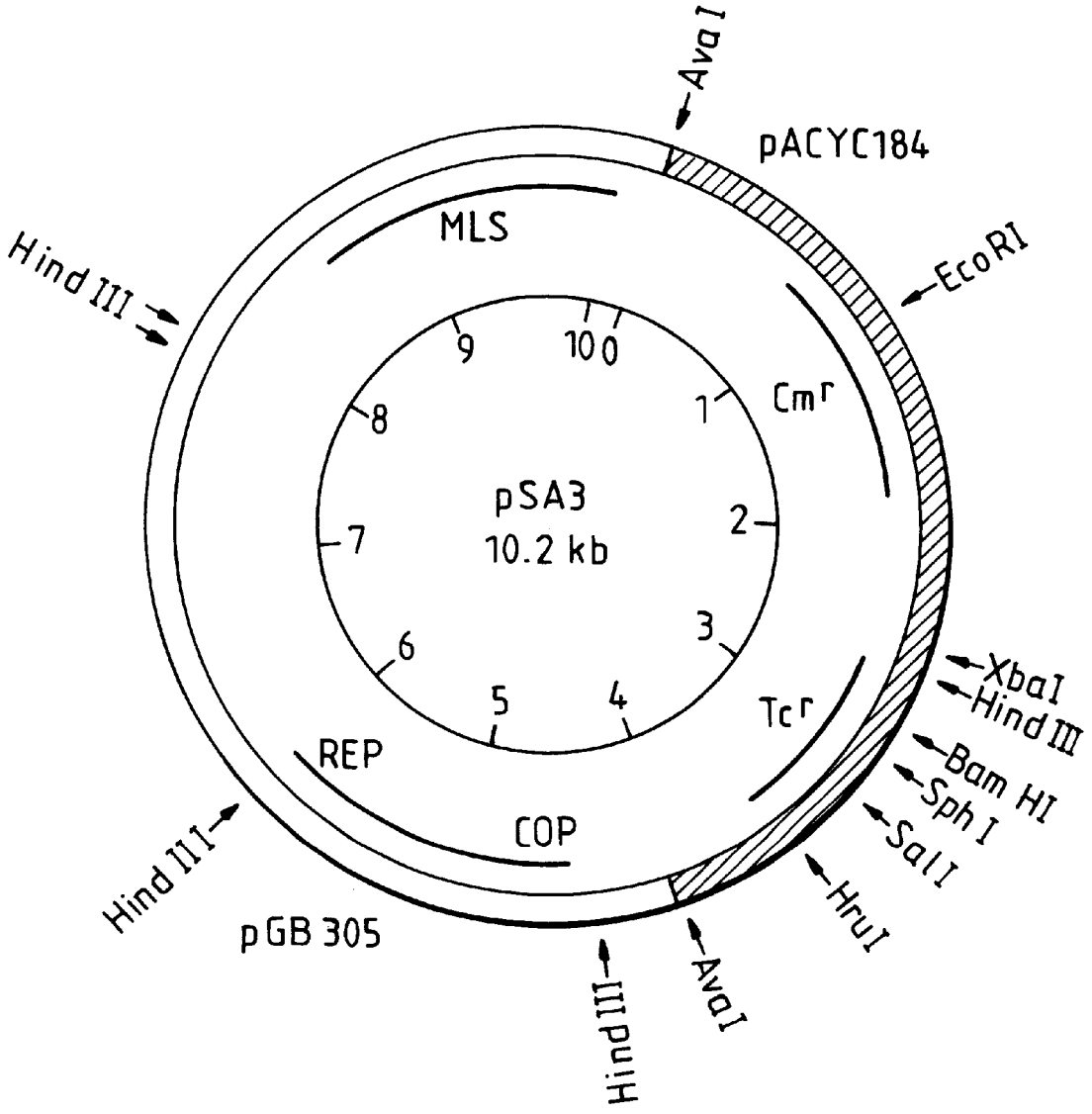
FIG. 1. Restriction map of plasmid pSA3. Symbols and abbreviations: The E. coli plasmid pACYC184 (the shaded region); the Streptococcal plasmid pGB305 (the unshaded region); MLS, macrolide linocosamide streptogramin B resistance; Cm' chloramphenicol resistance: Tc', tetracycline resistance: REP, replication region: COP, copy control region. (Taken from Ref. #4).

The present invention will be exemplified herein in terms of preferred embodiments for the isolation and use of [DNA segments comprising sequences encoding the HA synthase gene] *the recombinant DNA segment identified in FIG. 5* from Streptococcal sources. However, it will be appreciated by those of skill in the art that in light of the present disclosure the invention is also applicable to the isolation and use of the [HA synthase enzyme] *recombinant DNA segment identified in FIG. 5* from virtually any source, such as Streptococcus equisimilis, other group A or group C streptococcal strains or eukaryotic sources such as dermal or synovial fibroblasts, trabecular-meshwork cells or rooster comb mesodermal cells which contain [HA synthase encoding DNA] *the recombinant DNA segment identified in FIG. 5* that is actively transcribed (and is a suitable source of mRNA for the preparation of cDNA libraries).

The preferred application of the present invention to the isolation and use of [Streptococcal HA synthase DNA] *the recombinant DNA segment identified in FIG. 5* involves generally the steps of (1) isolation of Streptococcal genomic DNA; (2) partial restriction enzyme digestion of the genomic DNA with an enzyme such as EcoRI (selected enzyme not crucial) to provide DNA having an average length of up to 15 kb; (3) ligation of the partially digested DNA into a selected site within an antibiotic resistance gene in a pSA3 vector; (4) transfection of host Streptococcal or E. coli cells with the recombined vector; and (5) selection of colonies expressing [HA synthase or HA itself] *the recombinant DNA segment identified in FIG. 5 or HA itself* through the application of specially designed screening protocols. Following identification of a clone which contains the [HA synthase gene] *recombinant DNA segment identified in FIG. 5*, one may desire to reengineer the [HA synthase gene] *recombinant DNA segment identified in FIG. 5* into a preferred host/vector/promoter system for enhanced production of HA. Through application of the foregoing general steps, the inventors have succeeded in identifying and selecting two clones, one of which is believed to contain the [HA synthase gene] *recombinant DNA segment identified in FIG. 5* in a manner which allows it to produce HA. Table 1 summarizes the results obtained regarding the characterization of the two clones picked. One of these clones, clone 1, appears to be making both an HA-binding a protein, which is believed to be the [HA synthase] *product of the recombinant DNA segment identified in FIG. 5*, and HA. The fact that supplementing the media with the two precursor sugars confers the ability of clone 1 cells to bind $^{125}$I-PG is good evidence that these cells are capable of making HA.

Through application of the foregoing general steps, the inventors have succeeded in identifying and selecting two clones, one of which is believed to contain the HA synthase gene in a manner which allows it to produce HA. Table 1 summarizes the results obtained regarding the characterization of the two clones picked. One of these clones clone 1, appears to be making both an HA-binding protein, which is believed to be the HA synthase, and HA. The fact that supplementing the media with the two precursor sugars confers the ability of clone 1 cells to bind $^{125}$I-PG is good evidence that these cells are capable of making HA.

TABLE 1

CHARACTERIZATION OF TWO CLONES ISOLATED

| | Analyses | HB101 | D181 | Clone 1 | Clone 2 |
|---|---|---|---|---|---|
| 1. | Alcian blue staining | − | + | + | + |
| 2. | "Fried-egg" morphology of clones | − | + | + | + |
| 3. | Viscosity of culture supernatant | − | + | +/− | − |
| 4. | CPC-precipitability of culture medium | − | + | + | +/− |
| 5. | Presence of cell-surface HA ($^{125}$I-PG binding) | − | + | + | − |
| 6. | Presence of cell-surface HA-binding activity ($^{125}$I-HA binding) | − | N.D. | + | − |
| 7. | Presence of HA in culture medium assessed by: | | | | |
| | (a) Strep HAase | N.D. | N.D. | +/− | − |
| | (b) competition assay | − | + | − | − |

N.D. = Not determined

GENERAL OVERVIEW

A. Cloning of [Hyaluronate Synthase Gene] *the Recombinant DNA Segment Identified in FIG. 5*

Genomic DNA from the Streptococcus equisimilis strain D181 was isolated from bacteria following hyaluronidase treatment, chloroform/isoamyl extraction and ethanol precipitation. Conditions were determined for achieving an appropriate partial restriction enzyme digestion, such as would provide fragments on the order of 15 kb in length, with EcoRI enzyme. The partially digested Streptococcal DNA was ligated with fully digested pSA3 DNA, which was fully digested with EcoRI to generate compatible sites.

The pSA3 vector has been used by Dao and Ferretti (4) to clone the streptokinase gene from Streptococcus mutans and express the gene in E. coli, pSA3 can accommodate up to 15 kb of DNA insert and has multiple cloning sites in the chloramphenicol and tetracycline resistance genes. Arbitrarily, the EcoRI site in the chloramphenicol resistance gene was used to construct the genomic library. It is believed to be important to provide a DNA fragment encoding a full length or essentially full length enzyme because the initial screening protocol requires expression of a functional [enzyme] *recombinant DNA segment identified in FIG. 5* which would then synthesize HA.

Screening of Transformants

The primary screening protocol took advantage of the fact that alcian blue interacts with polyanionic molecules such as HA (23,31). A filter paper method of immobilizing bacterial colonies was employed followed by staining the filters with alcian blue. A second screening protocol using a labeled proteoglycan to detect the presence of [HA synthase] *the product of the recombinant DNA segment identified in FIG. 5* was useful as well. Such a screening protocol involves the binding of a radiolabeled, commercially available proteoglycan to intact cells to identify the presence of HA bound to the [HA synthase] *product of the recombinant DNA segment identified in FIG. 5.*

C. Further Characterization of the Putative HA-Screening Clones

Clones selected from the initial screening were characterized through the use of one or more biochemical tools for detecting HA on the cell surface and in the culture medium. The HA-binding proteins, e.g., rat chondrosarcoma proteoglycan, hyaluronectin, and a monoclonal antibody to HA, can be labeled with $^{125}$I and then used in direct binding assays. $^{125}$I-proteoglycan (PG) which is highly specific and binds very tightly to hyaluronic acid was used. A method (19) by which low molecular weight HA is uniquely modified at the reducing end to give an alkylamine derivative has been developed. This derivative can be used to prepare: (1) a Bolton-Hunter adduct that can be radioiodinated or biotinylated; (2) various affinity reagents, e.g., HA-Sepharose; and (3) polyacrylamide cell culture surfaces.

I. Solid phase binding assay

The various transfected clones were grown to log phase, harvested, and the culture media saved for further analysis. The cells were washed and resuspended in PBS. Binding with $^{125}$I-labeled PG was done to determine if HA was present on the surface of the clones. Clones grown to stationary phase were also analyzed since it is not known at what stage of the growth cycle HA may be synthesized in HB101. Untransformed HB101 and D181 were used as negative and positive controls, respectively.

Figure 9:
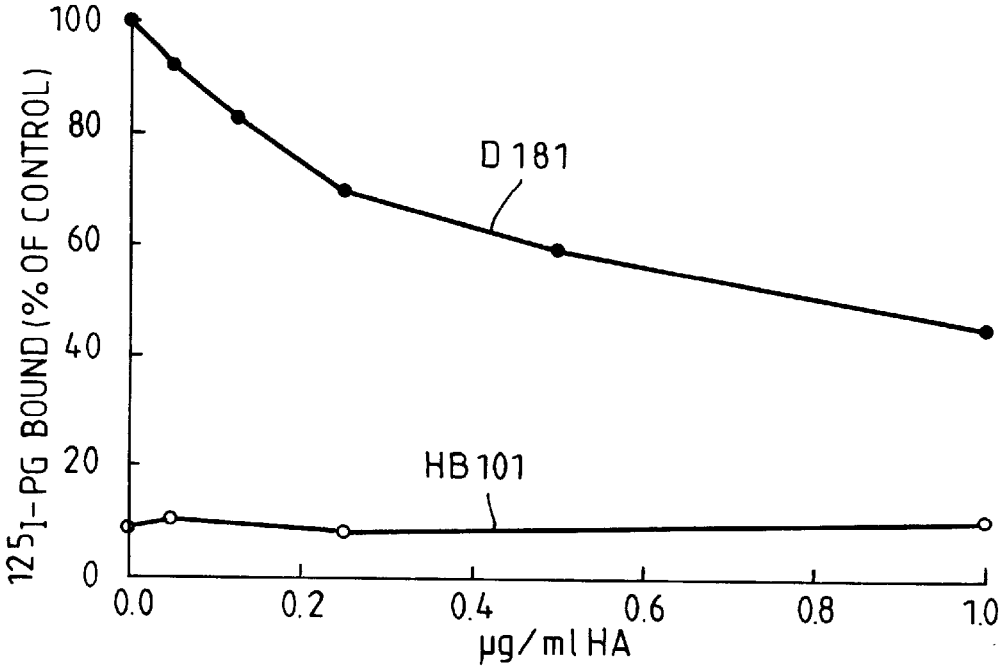
FIG. 9: Effect of unlabeled HA on the binding of $^{125}$I-proteoglycan to D181 and HB101. Bacterial cells ($5\times10^7$) were incubated for 1 hr at 4° C. with $^{125}$I-PG plus increasing amounts of unlabeled HA. The cells are washed three times with cold PBS to remove $^{125}$I-PG. Radioactivity of the cell pellets was determined in a gamma counter.

The culture fluid of the clones grown in a chemically defined medium was analyzed in competition experiments using fixed D181 cells (Table 1). If free HA is present in the culture media, it will compete for the binding of $^{125}$I-PG to HA on the surface of D181 cells. This is a very sensitive assay since as low as 200 ng of HA will decrease the binding of $^{125}$I-PG by about 30% (FIG. 9). No free HA was detected in culture fluid from either clone.

In identifying positive clones, a functional [hyaluronate synthase] *recombinant DNA segment identified in FIG. 5* is required so that HA can be synthesized and expressed on the cell surface or secreted into the culture medium. Even where negative results are obtained for certain of the foregoing assays, it is nonetheless possible that the [enzyme is] *recombinant DNA segment in FIG. 5 is* present but may not be functional or only functional at a very low level. Since the [synthase is] *product of the recombinant DNA segment in FIG. 5 is* an HA-binding protein, a method to detect its presence is through binding assays with $^{125}$I-HA (18). Clone 1 but not clone 2 was found to bind $^{125}$I-HA (Table 1), a property that was not found with the recipient HB101 E. coli strain. Thus, it is considered to be important that one carry out a variety of different assay procedures in order to confirm the results. Ultimately, as discussed below, one will desire to conduct DNA sequencing analyses of any clones thought to contain [HA synthase DNA] *the recombinant DNA segment identified in FIG. 5.*

2. Streptomyces hyaluronidase treatment of culture media

It may be desirable to further characterize the culture media by treatment with hyaluronidase (Streptomyces HAase) from Strepromyces hyalurolyticus. This enzyme has the advantage of being specific for HA alone and not the other glycosaminoglycans (16,24). This enzyme carries out an elimination reaction which results in the production of double bonds at the nonreducing end of HA. The unsaturated oligosaccharides produced can then be monitored by measuring the absorbance at 232 nm by a spectrophotometric assay.

3. Protease treatment of culture media

Depending on the post translational configuration of the *product of the* recombinant [HA synthase] *DNA segment identified in FIG. 5,* it is possible that the HA released into the medium will not be accessible to $^{125}$I-PG or Streptomyces HAase, e.g., due to HA's association with HA-binding proteins or cell wall fragments also produced by the bacteria. This could interfere with the initial screening or characterization of HA producing cells or clones. To potentially circumvent this possibility, one may desire to treat the culture media with a protease such as trypsin to eliminate proteins that may mask HA's proteoglycan binding sites or Streptomyces HAase cleavage sites. A trypsin inhibitor can further be used to stop the reaction before conducting the competition assays.

4. Sequencing of the [hyaluronate synthase gene] *recombinant DNA segment identified in FIG. 5*

After [a putative HA synthase gene] *the recombinant DNA segment identified in FIG. 5* has been cloned, one will desire to perform restriction mapping and DNA sequence analysis (e.g., by the dideoxy method (22)). Both the DNA and the deduced amino acid sequence can then be compared with known sequences to determine homologies with known proteins. The amino acid sequence of the protein will reveal the nature of the various domains, e.g., cytoplasmic, membrane-spanning, and substrate binding domains, and give important information in terms of approaches to improving the structure of the enzyme through genetic engineering techniques.

The [synthase gene] *recombinant DNA segment identified in FIG. 5* should be excised from the initial vector employed for cloning and put into another plasmid that is under the control of a strong promoter such as the lac promoter to overproduce the [enzyme] *product*. In accordance with the invention, such [as] *an* overproducing strain can be used [both] as a means of producing HA [and as a source of the enzyme, HA synthase].

The [enzyme] *recombinant DNA segment identified in FIG. 5* itself will find utility for in vitro applications, such as production of HA in an enzyme reactor. Such a solid phase reactor system could also incorporate the enzymes needed to synthesize the two sugar nucleotide precursors (e.g., UDP-GlcNAc pyrophosphorylase, UDP-GlcUA pyrophosphorylase and nucleoside diphosphokinase) from the sugar-1-phosphates, UDP and ATP. The [enzyme] *recombinant DNA segment identified in FIG. 5* can be used as well for the production of secondary reagents such as antibodies for screening purposes. To isolate the protein, the bacterial host should be disrupted, for example, by cavitation or by sonication, and cell extracts and membrane fractions prepared. Cell fractionation should be conducted in order to determine the fraction which contains the enzyme activity. Since the [synthase] *recombinant DNA segment identified in FIG. 5* is an HA-binding protein, it is possible to use an affinity column such as HA-Sepharose to isolate the [enzyme] *product of the recombinant DNA segment identified in FIG. 5* from the rest of the proteins in the cell extract or membrane fractions.

If in the particular construct which is developed the [enzyme] *product of the recombinant DNA segment identified in FIG. 5* is localized in the bacterial membrane, which is the expected location, it will be necessary to solubilize the preparation with a detergent before affinity chromatography. Testing of various detergents for the ability to maintain the [enzyme] *product of the recombinant DNA segment identified in FIG. 5* in its active form will be done. The eluted fractions from the affinity column are preferably analyzed by nondenaturing and by SDS polyacrylamide gel electrophoresis.

One may also desire to characterize the [Streptococcal or other HA synthases] *product of the recombinant DNA segment identified in FIG. 5* in terms of [their] *its* kinetics and physical and chemical properties. The parameters, $K_m$ and $V_{max}$, are determined from a double reciprocal plot of the velocity of the reaction versus substrate concentration (Lineweaver-Burke plot). Properties which may be of interest may include the [enzyme's] *product of the recombinant DNA segment identified in FIG. 5's* thermostability, optimum pH for activity, effects of various ions, and effects of various inhibitors. Isoelectric focusing will be used to determine [the] *its* isoelectric point [of the synthase]. Understanding these factors would provide basic information that may further allow one the ability to better determine what alterations in [their] *its* primary sequence can provide additional advantages.

By appropriate modification of the *recombinant* DNA segment [comprising the gene for HA synthase] *identified in FIG. 5* (e.g., deletion of membrane spanning domain of the protein), the [enzyme] *product of the recombinant DNA segment identified in FIG. 5* can be converted to a form that may be secreted by the transfected bacterial host. This [enzyme] *product of the recombinant DNA segment identified in FIG. 5* in soluble form, if still active in the ability to synthesize HA, would provide substantial improvement in the ease of purification of this [modified enzyme] *product* and in its potential utility [in an enzyme reactor system] for the in vitro production of HA.

D. Typical Genetic Engineering Methods Which May be Employed

If cells without formidable cell membrane barriers are used as host cells, transfection is carried out by the calcium phosphate precipitation method as described by Graham and Van der Eb (27). However, other methods may also be used for introducing DNA into cells such as by nuclear injection, protoplast fusion or by the Biolistic™ Bioparticle delivery System recently developed by DuPont (6). The advantage of using this system is a high transformation efficiency.

If prokaryotic cells or cells which contain substantial cell wall constructions are used, the preferred method of transfection is calcium treatment using calcium chloride as described by Cohen et al. (50).

Construction of suitable vectors containing the desired coding and control sequences employ standard ligation techniques. Isolated plasmids or DNA fragments are cleaved, tailored, and religated in the form desired to construct the plasmids required.

Cleavage is performed by treating with restriction enzyme (or enzymes) in suitable buffer. In general, about 1 ug plasmid or DNA fragments are used with about 1 unit of enzyme in about 20 ul of buffer solution. (Appropriate buffers and substrate amounts for particular restriction enzymes are specified by the manufacturer.) Incubation times of about 1 hour at 37° are workable. After incubations, protein is removed by extraction with phenol and chloroform, and the nucleic acid is recovered from the aqueous fraction by precipitation with ethanol.

If blunt ends are required, the preparation is treated for 15 minutes at 15° C. with 10 units of Polymerase I (Klenow), phenol-chloroform extracted, and ethanol precipitated.

For ligation approximately equimolar amounts of the desired components, suitably end tailored to provide correct matching are treated with about 10 units T4 DNA ligase per 0.5 ug DNA. (When cleaved vectors are used as components, it may be useful to prevent religation of the cleaved vector by pretreatment with bacterial alkaline phosphatase.)

For analysis to confirm correct sequences in plasmids constructed, the ligation mixtures are used to transform E.

coli K 12 strain 294 (ATCC 31446), and successful transformants selected by ampicillin or tetracycline resistance where appropriate. Plasmids from the library of transformants are then screened for bacterial colonies that exhibit HA production. These colonies are picked, amplified and the plasmids purified and analyzed by restriction mapping. The plasmids showing indications of a functional HA synthase gene will be further characterized by sequence analysis by the method of Sanger et al. (22), Messing et al. (51), or by the method of Maxam et al. (52).

E. Host Cell Cultures and Vectors

In general, prokaryotes are preferred for the initial cloning of DNA sequences and construction of the vectors useful in the invention. It is anticipated that the best host cells may be Gram positive cells, particularly those derived from the group A and group C Streptococcal strains. Bacteria with a single membrane, but a thick cell wall such as staphylococci and Streptococci are Gram positive. Gram negative bacteria such as E. coli contain two discrete membranes rather than one surrounding the cell Gram negative organisms tend to have thinner cell walls. The single membrane of the Gram positive organisms is analogous to the inner plasma membrane of Gram negative bacterial.

The best host cells may be streptococcal strains that are mutated to become hyaluronidase negative or otherwise inhibited (53–55). These strains will support the amplification of the shuttle vector pSA3 and will not degrade the product HA secreted into the medium. Other streptococcal strains that may be useful as suitable hosts include S. pyogenes and S. zooepidemicus. Although E. coliis gram negative it may, nonetheless, be a useful host cell in many situations. E. coli HB101 was chosen as the initial recipient strain for transformation and cloning of the [HA synthase gene] *recombinant DNA segment identified in FIG. 5* because this strain has proven to be very useful in recombinant DNA studies. It is a widely used host and is specifically engineered for recombinant DNA work. Other E. coli strains may also be useful for expression of the shuttle vector pSA3 containing the [HA synthase gene] *recombinant DNA segment identified in FIG. 5*. For example, E. coli, K 12 strain 294 (ATCC No. 31446) may be useful. Other strains which may be used include E. coli B, and E. coli X 1776 (ATCC No. 31537). These examples are, of course, intended to be illustrative rather than limiting.

Prokaryotes may also be used for expression. For the expression of [HA synthase] *the product of the recombinant DNA segment identified in FIG. 5* in a form most likely to accommodate high molecular weight HA synthesis, one may desire to employ Streptococcal strains such as S. equisimilis, S. pyogenes or S. zooepidemicus. The aforementioned strains, as well as E. coli W3110 (F-, lambda-, prototrophic, ATCC No. 273325), bacilli such as Bacillus subtilis, or other enterobacteriaceae such as Salmonella typhimurium or Serratia marcescens, and various Pseudomonas species may also be used.

In general, plasmid vectors containing origins of replication and control sequences which are derived from species compatible with the host cell are used in connection with these hosts. The vector ordinarily carries an origin of replication, as well as marking sequences which are capable of providing phenotypic selection in transformed cells. For example, E. coli is typically transformed using pBR 322, a plasmid derived from an E. coli species (see, e.g., ref. 34). pBR 322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

Those promoters most commonly used in recombinant DNA construction include the B-lactamase (penicillinase) and lactose promoter systems (35–38) and a tryptophan (trp) promoter system (35,39). While these are the most commonly used, other microbial promoters have been discovered and utilized, and details concerning their nucleotide sequences have been published, enabling a skilled worker to ligate them functionally with plasmid vectors (40).

In addition to prokaryotes, eukaryotic microbes, such as yeast cultures may also be used. Saccharomyces cerevisiase, or common baker's yeast is the most commonly used among eukaryotic microorganisms, although a number of other strains are commonly available. For expression in Saccharomyces, the plasmid YRp7, for example, is commonly used (41–43). This plasmid already contains the trp1 gene which provides a selection marker for a mutant strain of yeast lacking the ability to grow in tryptophan, for example ATCC No. 44076 or PEP4-1 (44). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (45) or other glycolytic enzymes (46–47), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (48). Examples of such useful host cell lines are VERO and HeLa cells, Chinese hamster ovary (CHO) cell lines, and WI38, BHK, COS, and MDCK cell lines. Other particularly useful host cell lines may be derived from dermal or synovial fibroblasts, mesodermal cells of rooster comb or the tribecular-meshwork cells of the eye. Expression vectors for such cells ordinarily include (if necessary) an origin of replication, a promoter located at the 5' end of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, bovine papilloma virus and most frequently Simian Virus 40 (SV40). The early and late promoters of SV40 virus are particularly useful because both are obtained easily from the virus as a fragment which also contains the SV40 viral origin of replication (49). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, BPV) source, or may be provided by the host cell chromosomal replication mechanism. If the vector is integrated into the host cell chromosome, the latter mechanism is often sufficient.

EXAMPLE I

ISOLATION OF THE [HYALURONATE SYNTHASE] *RECOMBINANT DNA SEGMENT IDENTIFIED IN FIG. 5* GENE FROM STREPTOCOCCUS EQUISIMILIS STRAIN D181

1. Isolation of genomic DNA from D181

Genomic DNA was isolated from S. equisimilis strain D181 and purified by CsCl-ethidium bromide density ultracentrifugation as follows.

Streprococcus equisimilis strain D181 was obtained in lyophilized form from the Rockefeller University Collection. The bacteria were grown in brain heart infusion (BHI) broth. Large scale isolation of genomic DNA from D181 was performed using a modification of the method of Wilson (33). Briefly, 100-ml culture of D181 was grown to saturation, the cells were pelleted for 10 min at 4,000×g in a Beckman JA-20 rotor and the supernatant discarded. The cell pellet was resuspended in 10 ml of 0.1M NaOAc, pH 5, 0.15M NaCl containing 10 mg testicular hyaluronidase (Sigma) and incubated at 37° C. for 1 hr. The bacteria were pelleted, resuspended in 10 ml of TE buffer (10 mM Tris, 1 mM EDTA, pH 8) containing 10 mg lysozyme (Sigma) and incubated for another hour. Then, 0.5 ml of 10% SDS and 50 ul of 20 mg/ml proteinase K were added and the mixture again incubated at 37° C. for 1 hour.

After cell lysis, 1.8 ml of 5 M NaCl was added and incubated at 65° C. for 20 min. The mixture was extracted with an equal volume of chloroform/isoamyl alcohol (24:1) solution and centrifuged for 10 min. at 6,000×g at room temperature. To the aqueous phase was added 0.6 volume of isopropanol to precipitate DNA. The precipitate was washed with 70% ethanol and resuspended in 4 ml of TE buffer. Cesium chloride (4.3 g per 4 ml TE buffer) and 200 ul of 10 mg/ml ethidium bromide were added, and the mixture was transferred to polyallomer sealable centrifuge tubes (Seton Scientific). The tubes were centrifuged for 4 hr at 70,000 rpm, 15° C. The DNA band was removed using a syringe and ethidium bromide was extracted with CsCl-saturated isoamyl alcohol. The DNA solution was dialyzed overnight against 2 liters of TE buffer.

2. Isolation of plasmid DNA

Figure 2:
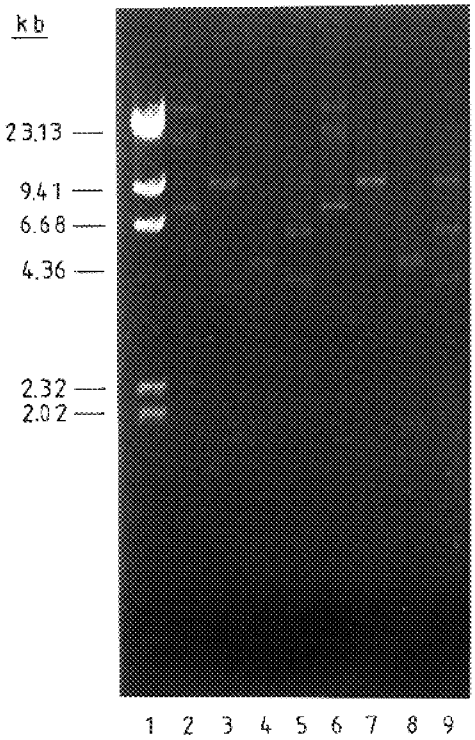
FIG. 2. Restriction enzyme analysis of the shuttle vector pSA3. pSA3-containing JM109 colonies were picked, the plasmid isolated by the boiling lysate method and aliquots cleaved with EcoRI, HindIII, and AvaI. Lanes are indicated in parentheses. HindIII-cut bacteriophage lambda markers (1); pSA3 digested with EcoRI (3 and 7), HindIII (4 and 8), and AvaI (5 and 9).

The cloning vector pSA3 is a 10.2-kb plasmid designed as a shuttle vector for use in both E. coli and Streptococcal hosts (4). The construction and use of this vector, which can accommodate up to about 15 Kb of DNA into one of multiple cloning sites into a CAM or TET resistance gene, is described in reference 4. FIG. 1 shows the restriction map of pSA3. To confirm the identity of the plasmid, aliquots were digested with restriction enzymes EcoRI, HindIII and AvaI, and the fragments analyzed using agarose gel electrophoresis (FIG. 2).

Large-scale isolation of plasmid DNA was performed using a modification of the alkaline lysis method of Maniatis et al. (12). Briefly, an overnight culture of pSA3-containing JM109 (gift of Dr. J. Ferretti, University of Oklahoma Health Science Center) was centrifuged at 7000 rpm at 4° C. for 15 minutes using a JA-10 rotor. The bacteria were lysed in Solution I (50 mM glucose; 25 mM Tris-HCl, pH 8; 10 mM EDTA) containing 5 mg/ml lysozyme. Then Solution II (1% SDS in 0.2N NaOH) was added and the mixture incubated for 10 min on ice. About ½ volume of ice-old 5M KOAc solution was added and the mixture incubated again for 10 min. The mixture was centrifuged at 17,000 rpm for 45 min at 4° C. using a JA-17 rotor. To the supernatant, 0.6 volume of isopropanol was added to precipitate DNA. The DNA was recovered by centrifugation at 8,000 rpm for 30 min at room temperature. The DNA pellet was washed with 70% ethanol and dissolved in TE buffer. The DNA was purified by CsCl-ethidium bromide density gradient centrifugation at 53,000 rpm for 18–20 hr at 20° C. using the Ti70 rotor.

Rapid, small scale isolation of plasmid DNA was carried out by the boiling lysate method of Maniatis (12) Briefly, 1.4 ml of an overnight bacterial culture in a 1.5-ml microfuge tube was centrifuged for 1 min. The supernatant was aspirated and the cell pellet was resuspended in 175 ul of STET buffer (8% sucrose, 0.5% Triton X-100, 50 mM EDTA and 10 mM Tris-HCl, pH 8). Lysozyme solution (25 ul, 10 mg/ml in 10 mM Tris-HCl, pH 8) was added and the tube was placed in a boiling water bath for 1 min. The mixture was microfuged for 10 min at room temperature and the pellet was removed from the bottom of the tube with a toothpick. Potassium acetate solution (25 ul, 5M) was added and the tube was microfuged for another 10 min. The supernatant was transferred to a new tube and isopropanol (250 ul) was added to precipitate nucleic acids for 15 min at room temperature. The nucleic acid precipitate was recovered by centrifugation for 15 min at 4° C., dried at 60° C. for 15 min and then resuspended in 50 ul of 1/10th TE buffer.

3. Construction of EcoRI genomic library

Figure 3:
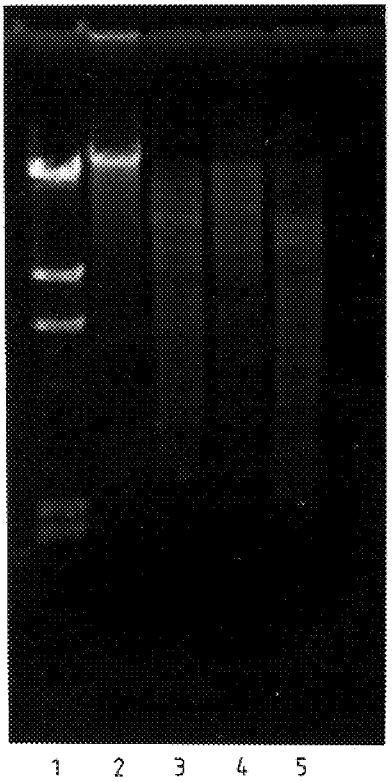
FIG. 3. Partial restriction enzyme digests of D181 genomic DNA. 0.5 ug of DNA was digested with 5 units of enzyme and incubated at 37° C. for 1 hr. Samples were run on 0.5% agarose gel. Lanes are indicated in parentheses. HindIII-digested bacteriophage lambda markers (1); untreated genomic DNA (2); DNA digested with EcoRI (3), BamHI (4), or SphI (5).

Restriction endonuclease EcoRI was selected to construct a genomic library. S. equisimilis strain D181 genomic DNA prepared as discussed above was partially digested with EcoRI (FIG. 3). The DNA fragments were purified by phenol/chloroform extraction and ethanol precipitation. pSA3 was completely digested with EcoRI and then dephosphorylated using calf intestinal alkaline phosphatase to prevent recircularization of the plasmid. Conditions for the ligation of chromosomal and plasmid DNAs were optimized. The ligation mixture was then used to transform competent HB101 cells. Transformed bacteria were plated on tetracycline-containing agar plates and screened. The specific details of the foregoing is set forth as follows.

D181 genomic DNA was partially digested with EcoRI, and pSA3 was linearized with EcoRI and dephosphorylated with calf intestinal alkaline phosphatase. Different ratios of the DNAs were mixed and T4 DNA ligase added in a total volume of 20 ul. The ligation mixtures were incubated at 15° C. overnight and aliquots were run on agarose gel to determine the ratio which gave optimal ligation. The buffer was added to a volume of 200 ul and 50 ul was used for each transformation.

Competent HB101 cells were prepared by the method of Maniatis (12). Room temperature 2× TY broth (15 ml) was inoculated with 1 ml of an overnight HB101 culture. The cells were grown to log phase (~$5\times10^7$ cells/ml) and centrifuged at 3,200 rpm for 5 min at 4° C. The cell pellet was gently resuspended in 10 ml of sterile Solution I (10 mM RbCl, 10 mM morpholinopropane sulfonic acid (MOPS), pH 7). The cells were centrifuged as above and the cell pellet resuspended in 10 ml of sterile Solution II (10 mM RbCl, 50 mM $CaCl_2$, 100mM MOPS, pH 6.5). The bacterial suspension was placed on ice for 30 min. The cells were centrifuged as above, the pellet was resuspended in 2 ml of Solution II and stored overnight at 4° C. for optimal efficiency.

To 200 ul of competent HB101 cells in a 1.5-ml microfuge tube, a 50-ul aliquot of ligation mixture and 2 ul of DMSO were added. The tube was placed on ice for 40 min, then incubated in a 43° C. water bath for 30–60 sec. The tube was placed immediately on ice, 1 ml of 2× TY broth Was added and incubated at 37° C. for 30 min. The transformation mixture was plated on selective medium at 50–200 ul per agar plate. The plates were incubated overnight at 37° C.

4. Screening

Since neither synthetic oligonucleotide probes for the [synthase gene] *recombinant DNA segment identified in FIG. 5* nor monoclonal antibodies against the [synthase] *product of the recombinant DNA segment identified in FIG. 5* are available, standard screening methods, such as colony hybridization, could not be used. Both the DNA sequence of the gene and the amino acid sequence of the protein were unknown. Thus, a novel approach to screening was devised in order to detect the presence of HA in bacterial colonies.

In an initial screening assay, transformant colonies were screened using the dye alcian blue, which stains polyanionic molecules such as HA (23,31). Filter paper was overlaid on agar plates with transformed colonies, incubated for an hour, removed and soaked in 2% acetic acid and 25% ethanol to fix the HA, and wash off bacterial colonies. The filters were dried and stained with 0.25% alcian blue (FIG. 4). Paper was used because HA is not immobilized by nitrocellulose filters.

An initial screen of about 3,000 transformants using the alcian blue dye screen gave two putative HA-synthesizing clones that stained with alcian blue and had a morphology similar to the parent strain D181. D181 colonies have a "fried-egg" appearance with a halo, whereas HB101 has no halo. Further studies indicated that the culture media from the two clones had cetyl pyridinium chloride (CPC)—precipitable material which included uronic acid, as assayed by the carbazole method of Bitter & Muir (3). These results are characteristic of HA.

Rapid, small scale isolation of plasmids from the 2 clones followed by digestion with EcoRI indicated that one clone (designated clone 1) had an insert size of about 2 kb, which corresponds to [the reported size of HA synthase,] a 52,000-dalton protein (18). The second clone, clone 2, had insert sizes of about 6 kb and 3.3 kb (FIG. 5) suggesting that two DNA fragments may have been joined end-to-end during the ligation reaction.

Figure 8:
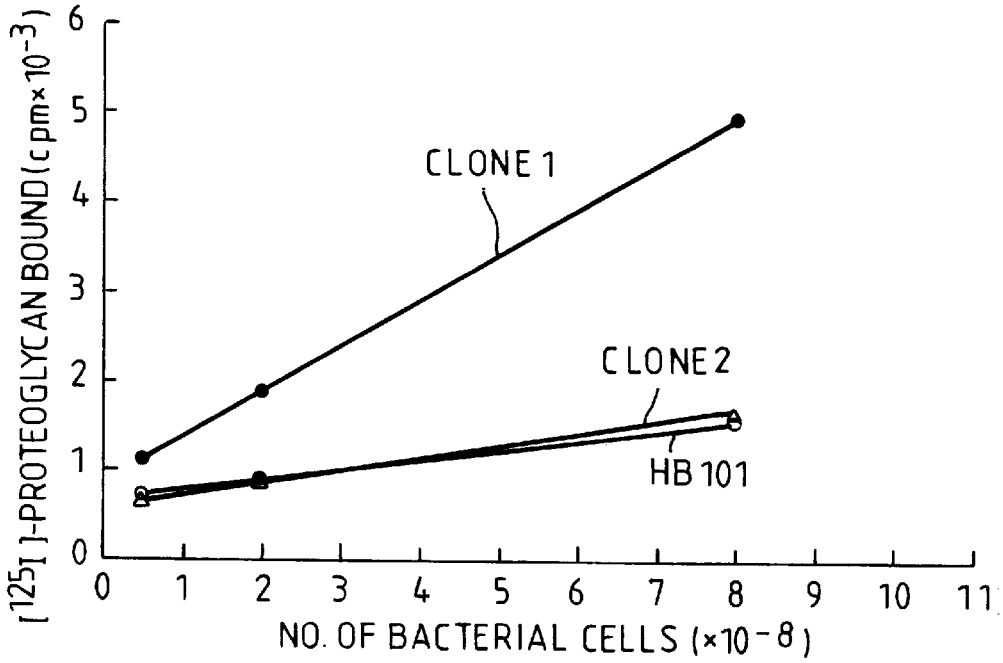
FIG. 8: Binding of $^{125}$I-PG to E. coli HB101, clone 1 and clone 2. Increasing number of cells were incubated with 1 ug/ml $^{125}$I-PG +/− 100 ug/ml HA for 3 hr at 4° C. Method as in FIG. 7. Open symbols: Total $^{125}$I-PG binding. Closed symbols: $^{125}$I-PG binding in the presence of 100-fold weight excess of unlabeled HA. Radioactivity of the cell pellets was determined in a gamma counter.

5. Development of a novel solid phase binding assay to detect the presence of HA In order to detect the presence of HA on transformed bacterial cells and in the culture supernatants, a new solid phase binding assay was also developed. This binding assay takes advantage of the specific binding of a proteoglycan (PG) monomer to the HA capsule on D181 cells. Radiolabeled PG ($^{125}$I) was allowed to bind to D181 Streptococcus cells, the cells were washed free of unbound $^{125}$I -PG, and the bound $^{125}$I-PG was determined in a gamma counter (FIGS. 8 and 9). This HA-PG specific binding can be competed off with both native ($10^6$Da) and small (60,000 Da) unlabeled HA. The extent of binding was studied by varying the amount of $^{125}$I-PG using a constant number of D181 cells. The optimal time of incubation was also determined to ascertain the time when binding is at equilibrium. Using a constant amount of $^{125}$I-PG (1 ug/ml) and an increasing number of D181 cells, binding started to saturate at 100–200 million cells. For subsequent binding assays, about 50 million log phase D181 cells have been employed.

a. Radioiodmation of the proteoglycan monomer

Rat chondrosarcoma proteoglycan monomer was obtained from ICN ImnunoBiologicals. It had a molecular weight of 2.5 million, 90% carbohydrate and 10% protein, and about 100 chondroitin sulfate chains (15). The proteoglycan was iodinated using Iodo-gen (Pierce) and Na$^{125}$I (Amersham) to a specific activity of $1–3\times10^6$ cpm/ug proteoglycan or 2650–6000 cpm/fmole. In the binding assays, about 1 ug/ml of the labeled proteoglycan was usually adequate to give a good signal. The $^{125}$I-PG was stable for about 2 weeks.

b. Fixation of D181 cells

Logarithmic phase D181 cells have their HA capsules intact, whereas stationary phase cells lose their capsules, since the bacteria make hyaluronidase late in the growth cycle (11,30). In order to minimize variability in day-to-day preparations of log phase D181, a method has been developed to fix the HA capsule on the Streptococcal cells. This has the advantage of providing an almost unlimited supply of a stable reagent, since cells can be fixed in large quantities and stored for a long time (up to several months) without losing their ability to bind proteoglycan. These fixed cells are useful as affinity reagents and in a wide variety of studies including: (1) identification of competitors of the HA-PG interaction, (2) isolation or purification of HA-binding proteins, [e.g., the HA synthase,] and (3) detection of soluble HA.

D181 cells in one liter of BHI broth were grown to logarithmic phase ($A_{550}$=0.2–0.4) and harvested by centrifugation at 4,000 rpm for 10 min at 4° C. The cells were washed twice with PBS containing 0.05% sodium azide. The final cell pellet was resuspended to 10% cell concentration in PBS containing 3% glutaraldehyde and 3% formaldehyde. The cell suspension was rotated for 90 min at room temperature. The cells were then washed three tines with PBS/azide and stored as a ~10% suspension in PBS/azide. The yield was about $8\times10^9$ fixed cells/ml for a starting bacterial culture of $A_{550}$=0.27.

c. Solid phase binding assay

The binding assay was performed either on live or fixed D181 cells. One ml of overnight D181 culture was added to fresh BHI broth and shaken vigorously (about 250 rpm) in a gyratory water bath shaker at 37° C. until logarithmic phase of growth ($A_{550}$==0.2–0.4). The cells were harvested by centrifugation at 4,000 rpm for 10 min at 4° C., washed once with cold PBS and resuspended in PBS containing 0.1% bovine serum albumin (BSA) at a concentration of $5\times10^8$ cells/ml. Aliquots of 100 ul of this cell suspension were put into 1.5-ml capacity microfuge tubes that had been blocked overnight with 2% BSA in PBS and washed twice with PBS. Binding mix (100 ul) containing PBS, 0.1% BSA, $^{125}$I-PG +/− HA or other competitors was then added and the tubes incubated on ice for 2–4 hrs with occasional mixing of the contents.

After incubation, one ml of cold PBS was added and the tubes microfuged [at 4°] for 30–60 sec. The cell pellets were washed twice with PBS by centrifugation and resuspension. The tips of the tubes were then cut off and counted in a gamma counter. Alternatively, the binding mixture was transferred to another tube containing 0.8–1.0 ml of an oil mixture composed of dibutyl phthalate:dioctyl phthalate (2:3). The tube was microfuged for 10 min and the aqueous and oil phases aspirated off. The tube tips were then cut off and counted. The assays were conducted in triplicate and standard deviations were typically less than 10%.

This assay was also performed on the culture medium from the clones being characterized (Table 1). The clones were grown in tetracycline-containing LB broth until logrithmic ($A_{500}$=0.2–0.4) or stationary ($A_{550}$>1.0) phase, then centrifuged and the clarified medium was saved. Binding assays as described above were carried out using increasing amounts of the test culture medium.

d. The Detection of HA or HA-binding activity on the clones

Figure 7:
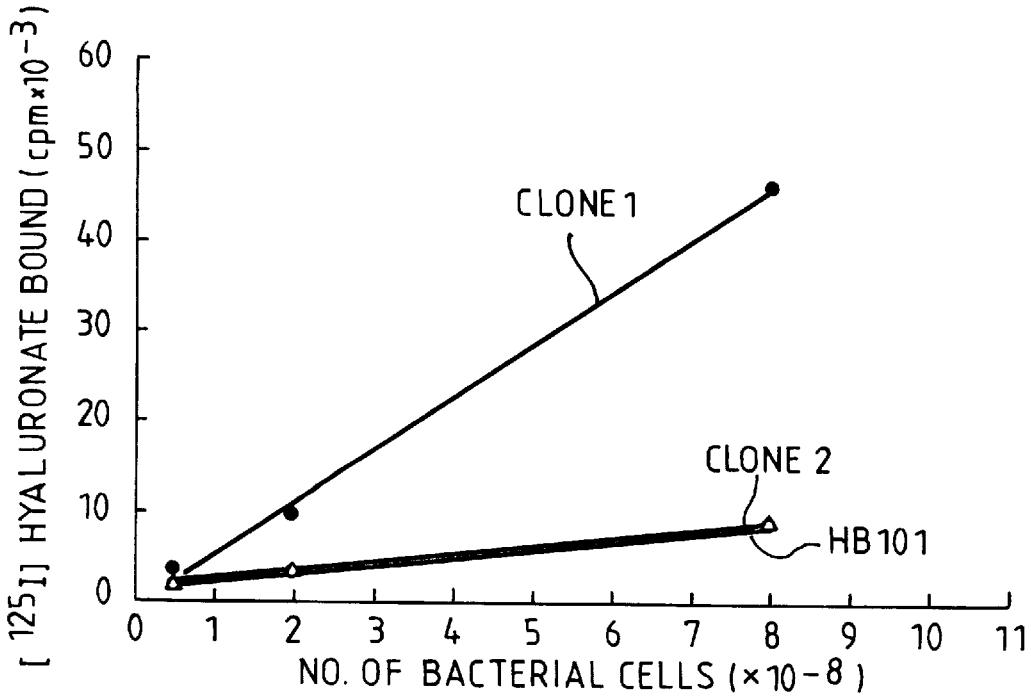
FIG. 7: Binding of $^{125}$I-HA to HB101, clone 1 and clone 2. An increasing number of cells were incubated with 6 ug/ml $^{125}$I-HA +/− 600 ug/ml unlabeled HA for 3 hr at 4° C. After incubation, the binding mixtures were transferred to tubes containing 0.8 ml of dibutyl phthalate:dioctyl phthalate (2:3) and microfuged for 10 min at 4° C. Open symbols: Total $^{125}$I-HA binding Closed symbols: $^{125}$I-HA binding in the presence of 100-fold excess of unlabeled HA. Radioactivity of the cell pellets was determined in a gamma counter.

HB101, clone 1 and clone 2 were grown to log phase in defined medium supplemented with GlcNAc and GlcUA. Cells were washed and their ability to bind $^{125}$I-HA was assessed to determine the presence of HA-binding proteins [(i.e., HA synthase, which may be present but not functional or functional at a very low level)]. FIG. 7 shows that $^{125}$I-HA bound significantly to clone 1, although this binding was not competed by 100-fold excess of unlabeled HA. There was no binding to HB101 and clone 2.

It was also determined whether by providing the cells with the precursors to make HA, the clones can make HA that is detectable by binding with $^{125}$I-PG. $^{125}$I-PG bound significantly to clone 1 and the binding was partially competed with unlabeled HA (FIG. 8). There was little or no binding to clone 2 and HB101. In another experiment, clone 1 grown in defined medium not supplemented with GlcNAc and GlcUA did not bind $^{125}$I-PG.

6. Media-based Assays

A. Development of defined media

Since HA needs to be analyzed in the culture medium, it is necessary to use a chemically defined medium rather than an undefined medium such as Luria Bertani (LB) broth. Aside from the required nutrients, glucuronic acid and N-acetylglucosamine, which are required for the synthesis of HA, are also supplied. HB101 and the two clones grow in the defined media with doubling times about twice that in LB broth.

An exemplary defined media which has been employed is as follows:

| | |
|---|---|
| 42.2 mM | $Na_2HPO_4$ |
| 22.0 mM | $KH_2PO_4$ |
| 18.7 mM | $NH_4Cl$ |
| 1.0 mM | $MgSO_4$ |
| 0.1 mM | $CaCl_2$ |
| 8.6 mM | NaCl |
| 1.0% (w/v) | glucose |
| 0.8% (w/v) | glucuronic acid* |
| 0.8% (w/v) | N-acetylglucosamine* |
| 0.2% (w/v) | arabinose |
| 0.2% (w/v) | galactose |
| 0.2% (w/v) | xylose |
| 0.2% (w/v) | mannitol |
| 200 ug/ml | proline |

-continued

| | |
|---|---|
| 200 ug/ml | leucine |
| 50 ug/ml | thiamine |

These values are the final concentrations. The pH is adjusted to pH 7.2 with NaOH. This medium was formulated for the E. coli HB101 strain.

This defined medium was used to enhance the ability to detect the presence of hyaluronic acid (HA) produced by the bacteria and secreted into the medium. The rationale for including the two sugars indicated by the * is that these are the precursors for the HA polymer. Their presence should increase the amount of HA able to be produced by the fermentation culture. In addition, use of a defined medium will increase the purity of the HA to be subsequently harvested in the culture medium.

b. Determination of uronic acid content

The carbazole method of Bitter & Muir (3) was used to determine uronic acid content in all samples. Glucuronic acid was used as the standard. Standards and samples in 500 ul were layered on top of frozen sodium tetraborate in concentrated $H_2SO_4$ (2 ml, 0.025M) and the tubes were shaken gently until room temperature was reached. Tubes were placed in a heating block at 100° C. for 10 min, cooled to room temperature and then 100 ul of 0.25% carbazole in ethanol was added. After mixing, the tubes were heated again at 100° C. for 15 min, cooled to room temperature and the absorbance at 535 nm measured. The color was found to be stable for 16 hours.

c. [Steptomyces] *Streptomyces* hyaluronidase assay

Figure 6:
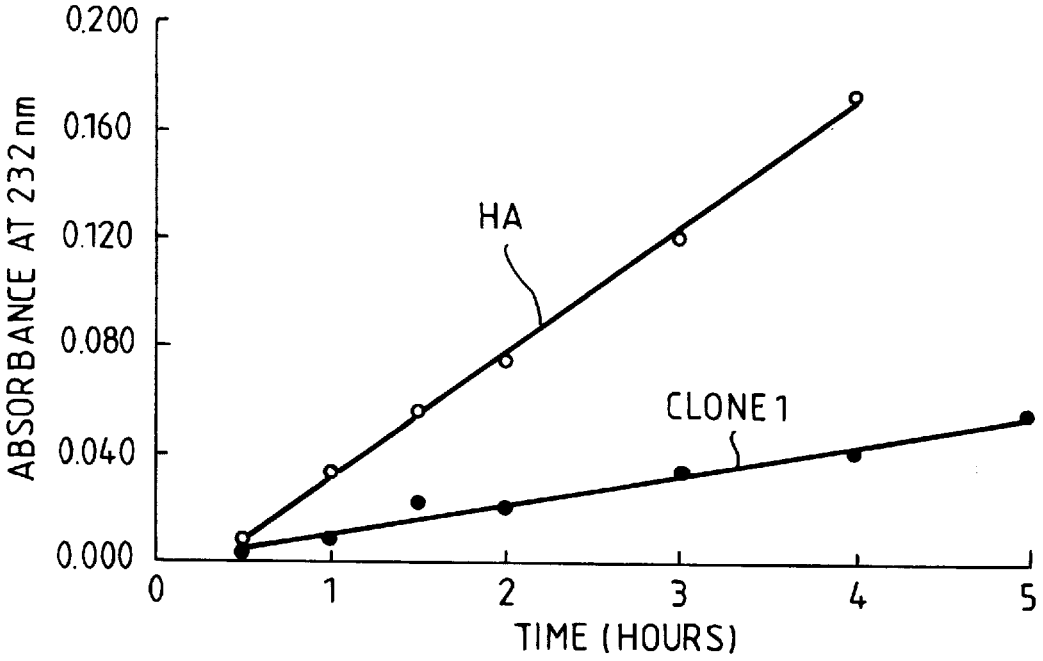
FIG. 6: Streptomyces hyaluronidase treatment of culture medium of clone 1. Glycosaminoglycans from culture medium of clone 1 were CPC precipitated, dissolved in 0.5M NaCl and ethanol precipitated. The precipitate was dissolved in assay buffer (20 mM NaOAc, pH6, containing 0.15M NaCl) and treated with 5 units of Streptomyces hyaluronidase. Increase in absorbance at 232 nm was measured with a spectrophotometer. HA that was processed identically was used as a positive control.

Glycosaminoglycans from culture media of clones 1 and 2 were isolated by CPC precipitation and analyzed by treatment with Streptomyces hyaluronidase, an enzyme specific for HA, by the procedures set forth in detail below. HA gave a linear increase in $A_{232}$ with time (FIG. 6). Generally, Clone 1 was found to give a modest increase in absorbance suggesting that HA was present However, some experiments for the presence of HA in transformed colonies have given negative results for both clone 1 and clone 2. The streptomyces hyaluronidase assay was performed as follows.

Media from cultures of the clones grown in LB broth were dialyzed against PBS overnight and then the glycosaminoglycans precipitated with 1 volume of 6% cetyl pyridinium chloride (CPC) for 1 hr at room temperature. The CPC precipitates were dissolved in 0.4M NaCl and 95% ethanol added until a precipitate formed. The precipitate was dissolved in water. Alternatively, culture media of the clones grown in a chemically defined medium were lyophilized. Known amounts were dissolved in assay buffer (20 mM NaOAc, pH6, containing 0.15M NaCl) and dialyzed overnight against the assay buffer.

Aliquots of the above solutions were treated with 5–10 turbidity reducing units of Streptomyces hyaluronidase (Sigma or Miles Labs.) in assay buffer and incubated in a 60° C. water bath. Samples were taken every hour and the absorbance at 232 nm measured using a spectrophotometer.

d. [Hyaluronate synthase] *Recombinant DNA segment identified in FIG. 5* assay

[Hyaluronate synthase] *The recombinant DNA segment identified in FIG. 5's* activity is assayed by the method of Sugahara et al. (28). Briefly, the incubation mixture (100 ul) contains 3.33 umol of $MgCl_2$, 0.5 umol dithiothreitol, 0.6 umol UDP-GlcNAc, 9–67 nmol of UDP-[U-$^{14}$C]GlcUA, and the [enzyme] protein to be assayed. Reactions at 37° C.

are initiated by addition of the enzyme and terminated by addition of 0.9 ml of cold 5.6% trichloroacetic acid (TCA). The radioactivity in HA associated with the [enzyme] *product of the recombinant DNA segment identified in FIG. 5* is determined by washing the TCA precipitate twice with 1.0 ml of 5% TCA, dissolving in 0.5 ml of 0.2N NaOH and liquid scintillation counting. The radioactivity in released HA chains is determined from the TCA supernatant by CPC precipitation and liquid scintillation counting.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting in kind or amount of the biological action. All such modification are intended to be included within the scope of the appended claims.

REFERENCES

The following references, to the extent that they provide exemplary procedural or other details supplementary to those set forth herein, are specifically incorporated herein by reference.

1. Barson (1986), J. Pediatr. Orthop., 6:346–348.
2. Benjamin et al. (1976), J. Pediatr., 89:254:256.
3. Bitter et al. (1962), Anal. Biochem. 4:330–334.
4. Dao et al. (1985), Appl. Envir. Microbiol., 49:115–119.
5. Dinn (1971), J. Ir. Med. Assoc., 64:50–51.
6. DuPont Biotech. Update, 4, #4, July 1989.
7. Hirsch et al. (1960), J. Exp. Med, 111:309–322.
8. Ishimoto et al. (1967), Biochim. Biophys. Acta, 148:296–297.
9. Kass et al. (1944), J. Exp. Med., 79:319:330.
10. Studier et al. (1989), Meth. Enzymol.: and Landschulz et al. (1989), Science, 243:1681–1688.
11. MacLennan (1956), J. Gen. Microbiol. 14:134–142.
12. Maniatis et al. (1982), Molecular Cloning: A Laboratory Manual,Cold Spring Harbor Laboratory, Cold Spring Harbor, N.Y.
13. Markovitz et al. (1959), J. Biol. Chem., 234:2343–2350.
14. Markovitz et al. (1962), Biol. Chem., 237:273–279.
15. Oegama et al. (1975), J. Biol. Chem., 250:6151–6159.
16. Ohya et al. (1970), Biochim. Biophys. Acta, 198:607–609.
17. Prehm (1983), Biochem. J., 211:191–198.
18. Prehm et al. (1986), Biochem J., 235:887–889.
19. Raja et al. Anal. Biochem, 139:168–177.
20. Rizkallah et al. (1988), J. Infect. Dis., 158:1092–1094.
21. Rotta (1988), APMIS Suppl., 3:3–7.
22. Sanger et al. (1977), Proc. Natl. Acad. Sci. USA, 74:5463–5467.
23. Scott et al. (1964), Histochemie. 4:73–85.
24. Shimada et al. (1980), J. Biochem., 88:1015–1023.
25. Siefkin et al. (1983), J. Clin. Microbiol., 17:386–388.
26. Stoolmiller et al. (1969), J. Biol. Chem, 244:236–246.
27. Graham et al. (1978), Virology, 52:546.
28. Sugahara et al. (1979), J. Biol. Chem., 254:6252–6261.
29. Triscott et al. (1986), J. Biol. Chem., 261:6004–6009.
30. van de Rijn (1983), J. Bacteriol., 156:1059–1065.
31. Whiteman (1973), Biochem J. 131:343–350.
32. Whitnack et al. (1981), Infect. Immun., 31:985–991.
33. Wilson (1987), "Large-Scale CsCl preparation of bacterial genomic DNA." Current Protocols in Molecular Biology. Greene Publishing associates & Wiley-Interscience, New York.
34. Bolivar et al., Gene, 2:95 (1977).
35. Chang et al., Nature, 375:615 (1978).
36. Itakura et al., Science, 198:1056 (1977).
37. Goeddel et al., Nature, 281:544 (1979).
38. Goeddel et al., Nucleic Acids Res., 8:4057 (1980).
39. EPO Appl. Publ. No. 0036776.
40. Siebwenlist et al., Cell, 20:269 (1980).
41. Stinchcomb et al, Nature, 282:39 (1979)
42. Kingsman et al., Gene, 7:141 (1979).
43. Tschemper et al., Gene, 10:157 (1980).
44. Jones, Genetics, 85:12 (1977).
45. Hitzeman et al., J. Biol. Chem., 255:2073 (1980).
46. Hess et al., J. Adv. Enzyme Reg., 7:149 (1968).
47. Holland et al., Biochemistry, 17:4900 (1978).
48. Tissue Culture, Academic Press, Kruse and Patterson, editors (1973).
49. Fiers et al., Nature, 273:113 (1978).
50. Cohen et al. (1972), Proc. Natl. Acad. Sci. USA, 69:2110.
51. Messing et al. (1981), Nucl. Acids Res., 9:309.
52. Maxam et al. (1980), Meth. Enzmol., 65:499.
53. European Patent Application EP144019.
54. European Patent Application EP266578.
55. European Patent Application EP244757.

What is claimed is:

1. A [DNA segment isolated from a eukaryotic or prokaryotic source comprising a sequence encoding hyaluronate synthase] *method for providing hyaluronic acid employing a recombinant DNA segment, comprising the steps of:*

(*i*) *providing recombinant Streptococcal host, wherein the recombinant Streptococcal host contains a plasmid comprising the DNA segment identified in FIG. 5 inserted therein;*

(*ii*) *culturing the recombinant Streptococcal host under conditions appropriate for the production of hyaluronic acid; and*

(*iii*) *separating the hyaluronic acid from the recombinant Streptococcal host.*

[2. The DNA segment of claim 1 wherein the encoded hyaluronate synthase comprises Streptococcal hyaluronate synthase.]

[3. A recombinant vector which incorporates a recombinant insert comprising a DNA segment in accordance with claim 1.]

[4. The recombinant vector of claim 3, further identified as a shuttle vector capable of replication in both a Streptococcal and E. coli host.]

[5. A recombinant host comprising the DNA segment of claim 1 or the vector of claim 3.]

[6. The recombinant host of claim 5, capable of expressing the DNA segment to produce hyaluronate synthase.]

[7. The recombinant host of claim 5, further defined as a Streptococcal or an E. coli host.]

[8. The recombinant host of claim 5, capable of expressing the hyaluronate synthase and producing hyaluronic acid.]

[9. The recombinant host of claim 5, further defined as a hyaluronidase negative host.]

[10. A method of providing hyaluronic acid comprising:

(a) providing a recombinant host bearing a recombinant DNA segment encoding a hyaluronate synthase enzyme and capable of expressing the enzyme;

(b) culturing the recombinant host in a medium under conditions appropriate for the production of hyaluronate synthase or hyaluronic acid; and (c) separating the hyaluronate synthase or hyaluronic acid from the recombinant host.]

* * * * *